(12) United States Patent
Venturini et al.

(10) Patent No.: US 11,882,768 B2
(45) Date of Patent: Jan. 23, 2024

(54) HANDSET FOR AN ULTRASONIC DEVICE

(71) Applicant: Orthofix S.R.L., Bussolengo (IT)

(72) Inventors: Daniele Venturini, Povegliano Veronese (IT); Mario Donnici, Bussolengo (IT)

(73) Assignee: Orthofix S.R.L., Verona (IT)

( * ) Notice: Subject to any disclaimer, the term of this patent is extended or adjusted under 35 U.S.C. 154(b) by 796 days.

(21) Appl. No.: 16/717,758

(22) Filed: Dec. 17, 2019

(65) Prior Publication Data

US 2020/0274055 A1    Aug. 27, 2020

(30) Foreign Application Priority Data

Feb. 21, 2019 (EP) .................................. 19158499

(51) Int. Cl.
*A61B 17/3203* (2006.01)
*H10N 30/20* (2023.01)
(Continued)

(52) U.S. Cl.
CPC ... *H10N 30/206* (2023.02); *A61B 17/320068* (2013.01); *H10N 30/88* (2023.02); *A61B 17/3203* (2013.01); *A61B 17/32037* (2013.01); *A61B 2017/00367* (2013.01); *A61B 2017/320084* (2013.01)

(58) Field of Classification Search
CPC .......... A61B 17/320068; A61B 2017/320084; A61B 17/3203; A61B 17/32037; A61B 2017/00367
See application file for complete search history.

(56) References Cited

U.S. PATENT DOCUMENTS 5,221,282 A * 6/1993 Wuchinich ............... A61N 7/00
606/99
5,318,570 A    6/1994 Hood et al.
(Continued)

FOREIGN PATENT DOCUMENTS

EP          2210565 A2    7/2010
WO    WO-9707755 A1 *  3/1997  ......... A61F 9/00745
(Continued)

OTHER PUBLICATIONS

European Patent Office, "European Search Report," for EP Application No. 19158499.4, dated Aug. 1, 2019.

*Primary Examiner* — Timothy J Neal
*Assistant Examiner* — Mitchell Brian Hoag
(74) *Attorney, Agent, or Firm* — Haynes and Boone, LLP

(57) ABSTRACT

A handset for an ultrasonic device for bone cement removal and/or osteotomy operations comprises a handset body which encloses ultrasound generating means including at least one piezoelectric transducer and a horn, connection means configured to connect the handset to a tool to which the ultrasounds generated by the ultrasound generating means are transmitted, a duct for circulation of a cooling medium, the duct extending at least partially on the outside of the handset, a triggering element whose activation causes the activation of the ultrasound generating means, and a control lever coupled to the handset body at a connection point, the control lever being configured to activate the triggering element by means of its movement about the connection point.

15 Claims, 10 Drawing Sheets

(51) Int. Cl.
  *A61B 17/32*  (2006.01)
  *H10N 30/88*  (2023.01)
  *A61B 17/00*  (2006.01)

(56) References Cited

U.S. PATENT DOCUMENTS

| | | | | |
|---|---|---|---|---|
| 6,017,354 | A * | 1/2000 | Culp | A61B 17/1626 604/22 |
| 6,139,561 | A | 10/2000 | Shibata et al. | |
| 2005/0209596 | A1* | 9/2005 | Daniels | A61B 17/2909 606/83 |
| 2007/0055228 | A1* | 3/2007 | Berg | A61B 17/320092 606/41 |
| 2014/0104070 | A1* | 4/2014 | Plaven | A61B 17/320092 340/815.45 |
| 2015/0142033 | A1* | 5/2015 | Stulen | A61B 17/320068 606/169 |
| 2015/0165240 | A1* | 6/2015 | Stoddard | A61B 17/32 606/171 |
| 2015/0306428 | A1* | 10/2015 | Darian | A61B 90/30 601/2 |
| 2017/0000512 | A1* | 1/2017 | Conlon | A61B 18/04 |
| 2017/0000513 | A1* | 1/2017 | Conlon | A61B 17/320068 |
| 2017/0056053 | A1* | 3/2017 | Dickerson | A61B 17/320068 |
| 2017/0172606 | A1 | 6/2017 | Rienstenberg et al. | |
| 2017/0172614 | A1 | 6/2017 | Scheib et al. | |
| 2017/0311974 | A1* | 11/2017 | Friedrichs | A61B 17/320092 |
| 2018/0014847 | A1* | 1/2018 | Parham | A61F 9/00745 |
| 2019/0008543 | A1* | 1/2019 | Scoggins | A61B 90/08 |
| 2019/0159793 | A1* | 5/2019 | Cotter | A61M 3/0279 |
| 2019/0247073 | A1* | 8/2019 | Cowley | A61B 17/320092 |
| 2019/0282293 | A1* | 9/2019 | Batchelor | A61N 7/00 |
| 2019/0357991 | A1* | 11/2019 | Stefan | A61B 34/30 |
| 2020/0093507 | A1* | 3/2020 | James | A61B 90/98 |

FOREIGN PATENT DOCUMENTS

| | | | |
|---|---|---|---|
| WO | WO 2012/061730 A1 | 5/2012 | |
| WO | WO-2019096929 A1 * | 5/2019 | A61B 1/00149 |

* cited by examiner

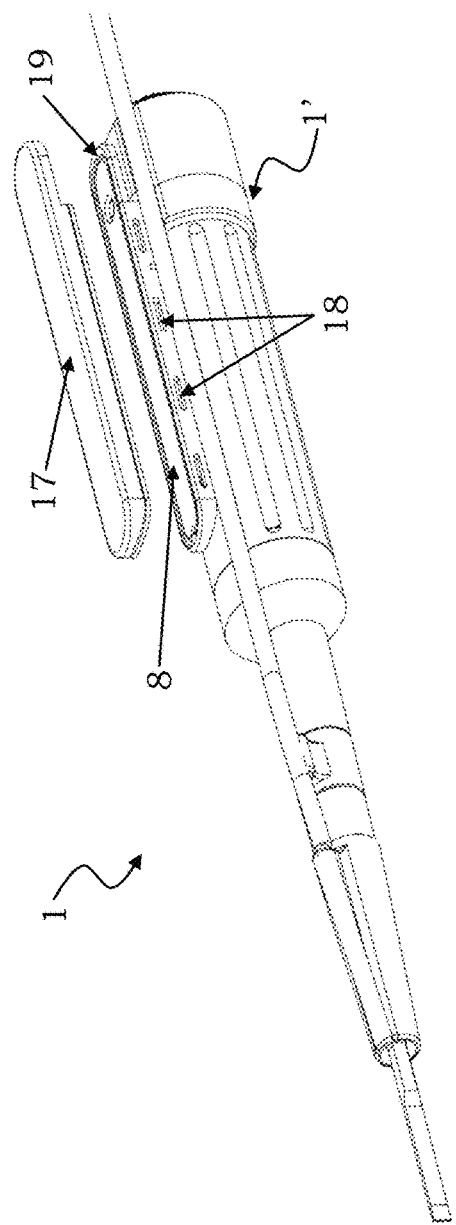
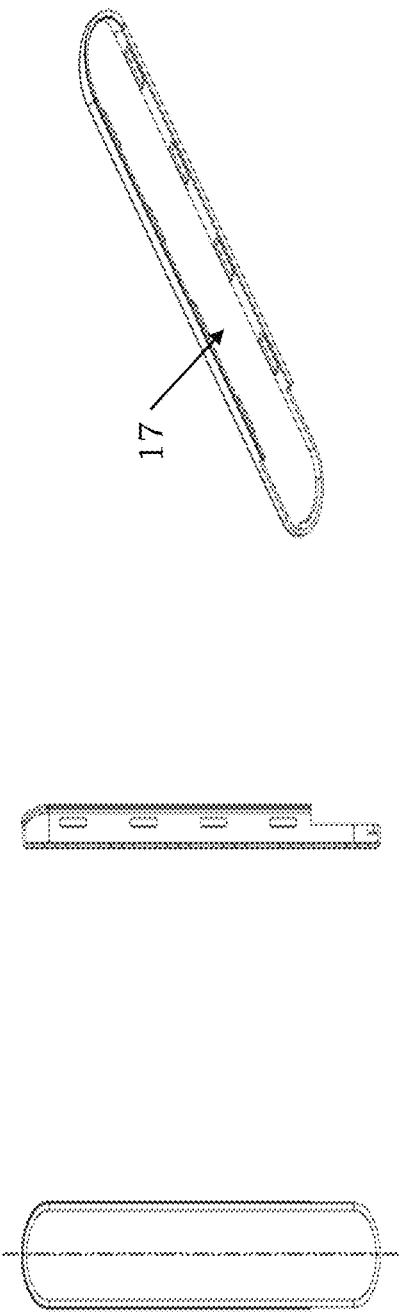
FIG. 9A FIG. 9B FIG. 9C FIG. 9D

HANDSET FOR AN ULTRASONIC DEVICE

BACKGROUND

Field of Application

The present disclosure relates to a handset for an ultrasonic device, in particular a handset which can be connected to a tool for performing bone cement removal and/or osteotomy operations, and the following description is provided with reference to this field of application with the sole aim of simplifying illustration thereof.

Description of the Related Art

As it is well-known in this technical sector, during prosthetic revision procedures there is often the need to remove bone cement consisting of polymethyl methacrylate (PMMA). This is a particularly delicate procedure and incorrect execution thereof risks causing serious damage to the bone tissue.

There are ultrasonic devices which are able to remove the bone cement by means of special tools to which ultrasounds are transmitted. This simplifies the removal of the bone cement during the prosthetic revision procedures since the action of the ultrasounds causes softening of the cement which keeps the implant in position. The tools are therefore positioned so as to collect and remove the softened cement from the host bone. This technique reduces the manual effort and allows the risk of bone fractures and perforations to be reduced.

Ultrasonic devices are also used in osteotomy operations involving resection of bone portions, where a blade is moved in a predefined manner by means of ultrasounds.

The known solutions generally envisage the presence of a generator to which a handset containing the ultrasound generating elements is connected, said generator allowing powering of the handset and setting of its operating parameters. The tools to which the ultrasounds are transmitted during the operations are then connected to the handset.

However, the solutions which are available nowadays have a number drawbacks, mainly due to the fact that the handling of the grip is not easy during operations, this complicating the work of the operators.

In particular, the handset generally has a handle which extends along its longitudinal axis, this on the one hand favouring some specific movements performed by the surgeon, but on the other hand it has the drawback that, if there is an activation pushbutton present on this handle, it is not easy to keep this pushbutton pressed during the operation. Furthermore, the presence of an activation pushbutton on the handle makes it difficult to provide the necessary seals able to withstand the sterilization processes.

In some known solutions the handset is operated by means of a pedal control, even though a manual control on the handle is preferable since it is easier to use and reduces the number of components in the operating theatre.

Another drawback which is often encountered in the known solutions is that it is not easy to adapt the handset to different types of operation, since very often the known handsets cannot be easily reconfigured.

It is therefore desirable to have a handset for an ultrasonic device which has functional and structural characteristics such as to be able to overcome the limitations and drawbacks which hitherto affect the known solutions, in particular such as to allow simpler and at the same time more effective and flexible use of the handset.

SUMMARY OF THE DISCLOSURE

The present disclosure provides a handset for an ultrasonic device having means which allow simpler and more efficient operation of the handset by the surgeon, while simplifying handling and use thereof during operations, as well as means which allow the handset to be easily reconfigured so that it may be adapted to different situations.

More in particular, an exemplary handset for an ultrasonic device for bone cement removal and/or osteotomy operations comprises a handset body which encloses ultrasound generating means comprising at least one piezoelectric transducer and a horn, connection means configured to connect the handset to a tool to which the ultrasounds generated by the ultrasound generating means are transmitted, a duct for circulation of a cooling medium, the duct extending at least partially on the outside of the handset, a triggering element whose activation causes the activation of the ultrasound generating means, and a control lever coupled to the handset body at a connection point, the control lever being configured to activate the triggering element by means of its movement about the connection point.

According to one aspect of the present disclosure, the triggering element may comprise a Hall effect sensor and a magnet arranged on the control lever, wherein the movement of the control lever about the connection point results in a variation of the relative distance between the Hall effect sensor and the magnet, causing activation of the ultrasound generating means.

Alternatively, the triggering element may be a pushbutton, in which the movement of the control lever about the connection point results in pressing contact of this control lever against this pushbutton, causing activation of the ultrasound generating means.

According to one aspect of the present disclosure, the connection means may comprise a threaded connection at the end of the horn of the ultrasound generating means.

According to another aspect of the present disclosure, the handset may comprise a first covering element configured to cover at least partially the horn, this first covering element being connected removably to the handset body.

According to another aspect of the present disclosure, the handset may comprise a second covering element configured to cover at least partially the tool to be associated with the handset, the second covering element being able to be connected removably to the first covering element.

In particular, the second covering element may comprise a connection element for the duct, the connection element being configured so that the cooling medium supplied by the duct is made to flow inside the second covering element. In other words, the connection element is an engaging means which allows the duct to be placed in fluid communication with the inside of the second covering element.

According to another aspect of the present disclosure, the duct may be associated removably with the handset.

According to another aspect of the present disclosure, the handset may comprise at least one luminous signalling element configured to indicate to the operator an operative condition of the handset.

In particular, the luminous signalling element may be housed inside the handset body and the control lever may be shaped so as to transmit and make visible the signal emitted by this luminous signalling element.

Even more particularly, the luminous signalling element may be an LED incorporated within the triggering element, or the luminous signalling element may be an LED which is connected to a printed circuit board and the emitted radiation of which is transmitted by a light guide arranged between the printed circuit board and the control lever.

According to another aspect of the present disclosure, the handset may also comprise a lighting element configured to illuminate the treatment zone. More specifically, the lighting element may be connected removably to the handset.

According to another aspect of the present disclosure, the handset may comprise a gripping system arranged substantially transversely with respect to the handset body, this gripping system being provided with a control element configured to operate a mechanical transmission which causes the movement of the control lever, and this gripping system being connected removably to the handset body.

In particular, the mechanical transmission may be of the cam type with a movement in the direction of the handset body and operated by the control element, the removable connection being realized by means of an eccentric ring nut provided at the top of a body which forms a handle.

According to yet another aspect of the present disclosure, the handset body may have a substantially cylindrical form and may extend around a longitudinal axis.

According to yet another aspect of the present disclosure, the handset may comprise a silicone covering element configured to cover the control lever, the covering element being connected to the handset body by means of fixing slots.

Finally, the ultrasound generating means may be configured to transmit ultrasounds both to tools used for the removal of bone cement and to tools used for osteotomy operations.

The features and advantages of the handset according to the disclosure will become apparent from the following description of an embodiment thereof, given by way of non-limiting example with reference to the accompanying drawings.

BRIEF DESCRIPTION OF THE DRAWINGS

In these drawings:

FIG. 9A shows a view of a handset according to an embodiment of the present disclosure; and FIGS. 9B, 9C, and 9D show details of the handset according to FIG. 9A.

DETAILED DESCRIPTION

Figure 1:
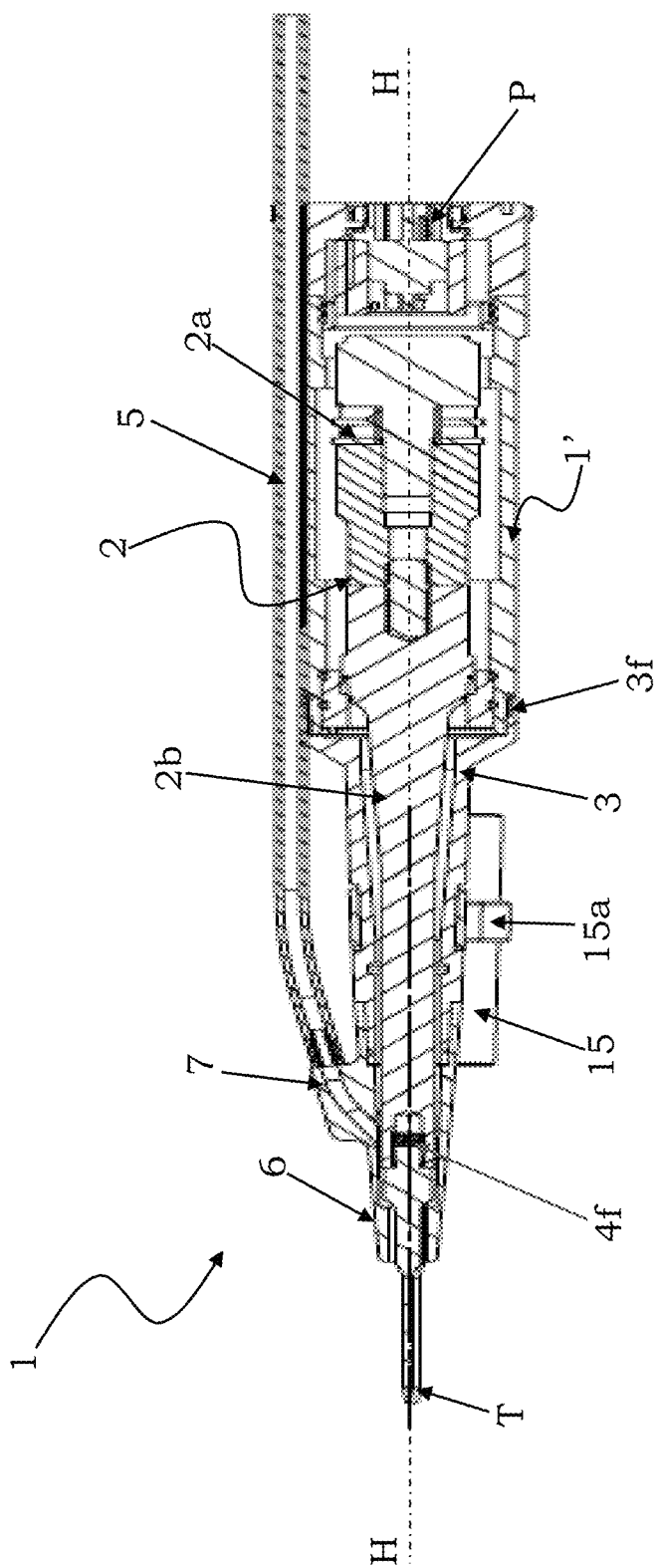
FIG. 1 shows a schematic cross-sectional view of a handset according to the present disclosure.

With reference to those figures, and in particular to the example of FIG. 1, a handset for an ultrasonic device according to the present disclosure is globally and schematically indicated with the reference number 1.

It is worth noting that the figures represent schematic views and are not drawn to scale, but instead they are drawn so as to emphasize the important features of the disclosure. Moreover, in the figures, the different elements are depicted in a schematic manner, their shape varying depending on the application desired. It is also noted that in the figures the same reference numbers refer to elements that are identical in shape or function. Finally, particular features described in relation to an embodiment illustrated in a figure are also applicable to the other embodiments illustrated in the other figures.

The handset 1 according to the present disclosure is used mainly to remove the bone cement during prosthetic revision procedures or also for the resection of bone portions during osteotomy operations.

The handset 1 comprises a handset body 1' which has a substantially cylindrical form and extends along a longitudinal axis H-H between a distal end (namely the end closest to the operator) and a proximal end (namely the end closest to the zone to be treated). The handset 1 therefore has a handle extending along the longitudinal axis H-H, favouring certain specific movements of the surgeon during the operations. The handle is also provided with grooves S which allow a more stable grip.

The handset body 1' encloses and acts as a protective element for ultrasound generating means 2 which include a piezoelectric transducer 2a and a horn 2b, as known in the art.

More specifically, the handset 1 is connected to a generator (not shown in the figures) by means of an electric cable, this electric cable being associated with the handset 1 by means of a suitable socket P provided preferably at the distal end of the handset body 1', in particular on the base of the handset body 1'.

The piezoelectric transducer 2a is configured to convert the electric energy from the generator into mechanical vibrations, generally in a frequency range varying from 0 to 100 MHz, preferably 20 kHz to 20 MHz.

The horn 2b is therefore configured to amplify and transfer the vibrations generated by the piezoelectric transducer 2a to a tool T connected thereto, as will be illustrated below. A booster arranged between the piezoelectric transducer 2a and the horn 2b is also envisaged.

Generally, the end of the horn 2b opposite to the piezoelectric transducer 2a projects from the handset body 1' and for this reason this projecting portion is covered at least partially by a first covering element 3 associated with the handset body 1'. In other words, the first covering element 3 acts as a protective element for the horn 2b.

More particularly, the first covering element 3 is connected removably to the handset body 1', for example by means of a suitable threaded connection 3f.

The first covering element 3 may take various forms. For example, it may have a groove for containing a sealing O-ring.

As mentioned above, the handset 1 comprises connection means 4 for connecting it to a tool T (also called probe) to which the generated ultrasounds are transmitted. Preferably, the connection means 4 are in the form of a threaded connection 4f at the proximal end of the horn 2b.

It is pointed out that the tools associated with the handset 1 may have different forms and functions and will not be described in the present detailed description, the form and functions of these tools in fact not limiting the present disclosure.

Furthermore, it is known that, during operation of the ultrasonic system, the temperature of the tool associated with the handset 1, as well as the temperature of the treated area, may reach high values which are potentially dangerous for the instrument and the patient. For this reason, the handset 1 according to the present disclosure comprises a duct 5 for circulation of a cooling medium which is sprayed onto the tool and the treated zone of the patient.

Advantageously, the duct 5 is associated with the handset 1 removably and extends at partially on the outside of the handset 1, in particular completely on the outside of the handset body 1'.

Figure 2A:
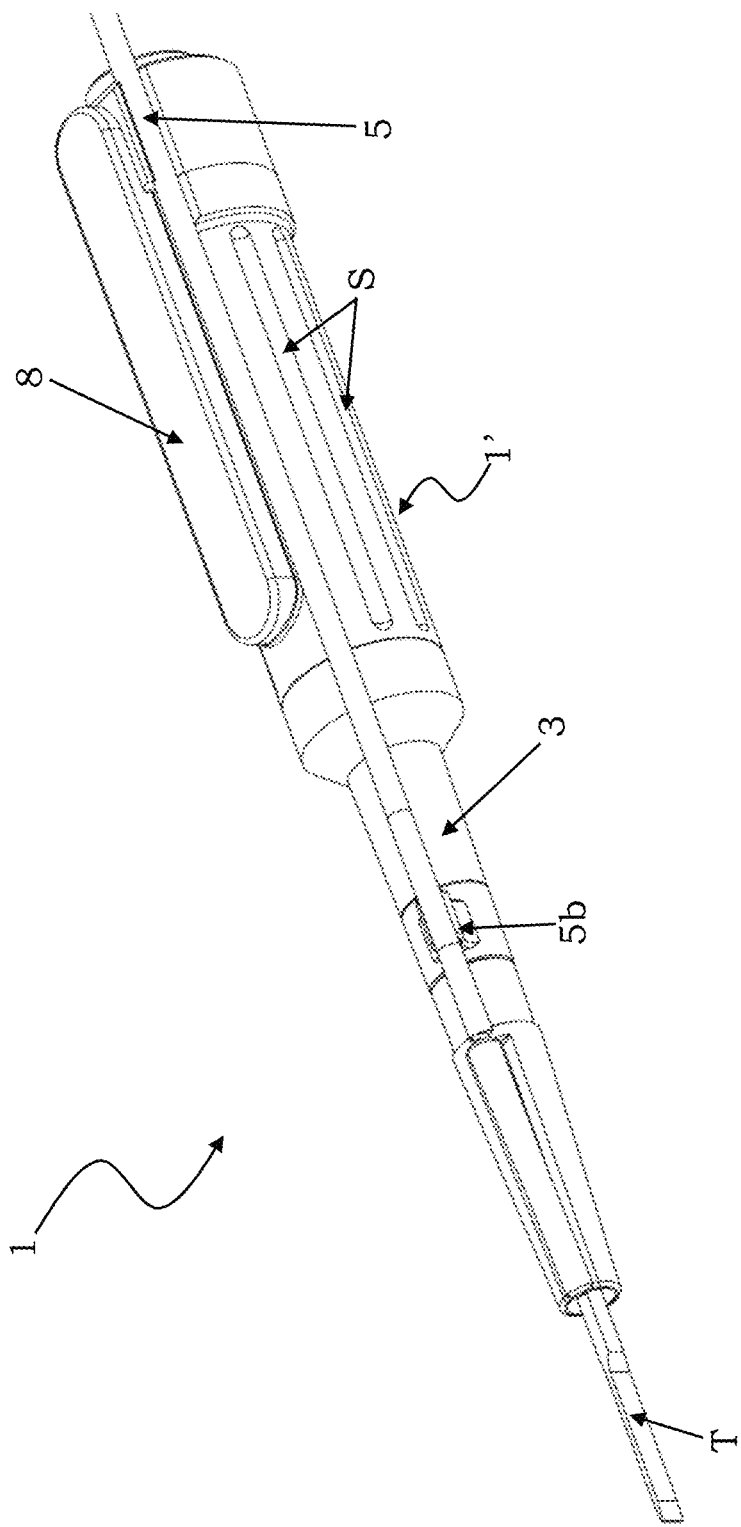
FIG. 2A shows a perspective view of a handset according to a preferred embodiment of the disclosure.

In a preferred embodiment, shown in FIG. 2A, the distal end of the handset 1' is shaped so as to have a recess for housing the duct 5.

Figure 2B:
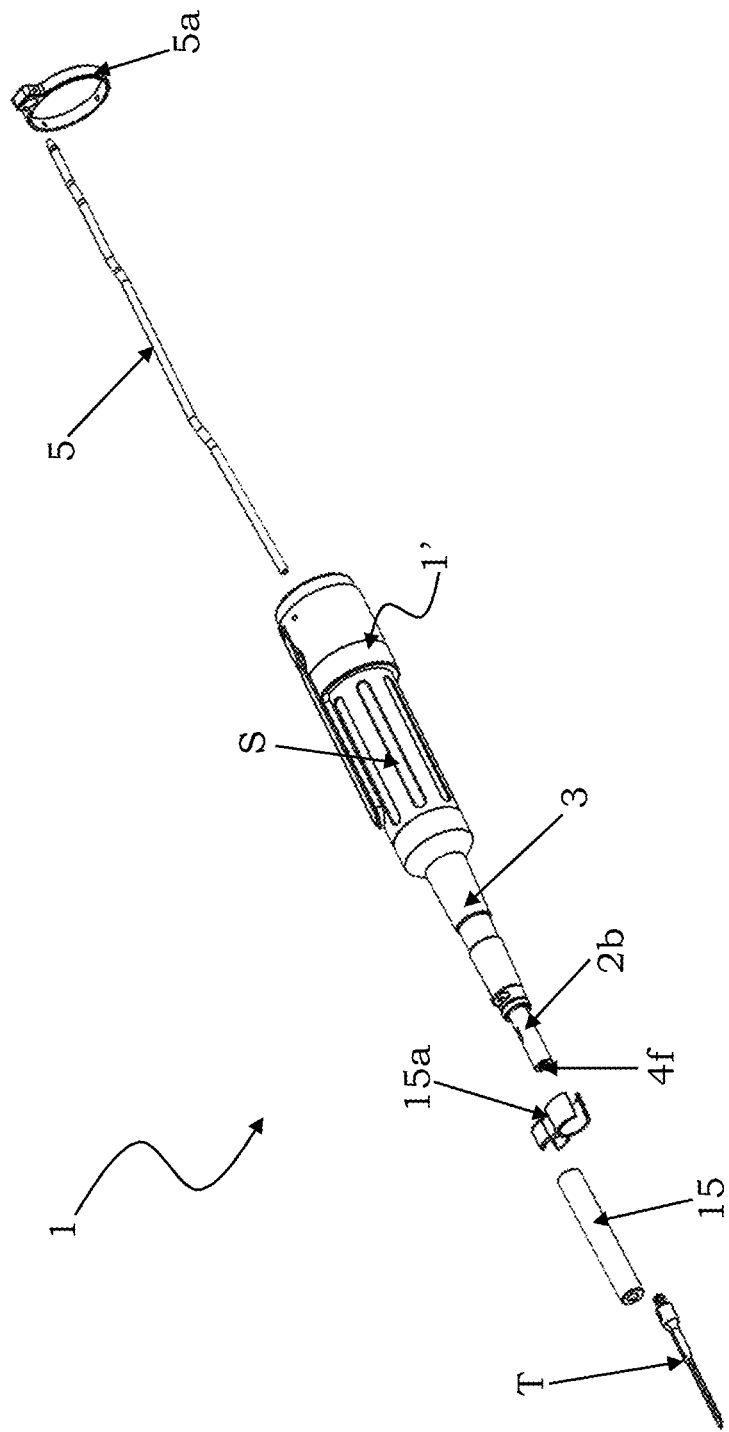
FIG. 2B shows an exploded perspective view of a handset according to an embodiment of the present disclosure.

In an alternative embodiment, shown in FIG. 2B, the duct 5 is associated removably with the handset body 1' by means of suitable engaging means 5a arranged at the distal end.

The embodiment in which the duct 5 is associated with (connected to) the handset 1 by means of a recessed part formed as one piece in the handset body 1' allows the engaging means 5a to be eliminated and therefore the handset 1 to be simplified.

In any case, the cooling medium is conveyed outside the handset 1 by means of the duct 5 towards the tool T and the treated area.

In an embodiment, the handset body 1' may also comprise a housing seat over its whole outer surface (and not only at the distal end) for housing the duct 5 and therefore reducing its overall volume, as will be illustrated further below.

The flow of the cooling medium (which normally consists of a physiological solution) is ensured by means of a peristaltic volumetric pump which is incorporated in the generator and able to control and meter the flowrate. The pump can be activated by the surgeon for example by means of pedal switch or by means of corresponding pushbuttons. By means of a series of pipes passing through the peristaltic pump it is therefore possible to connect the cooling medium container to the duct 5, the latter being able to convey the correct amount of cooling medium into the treatment zone.

Figure 3A:
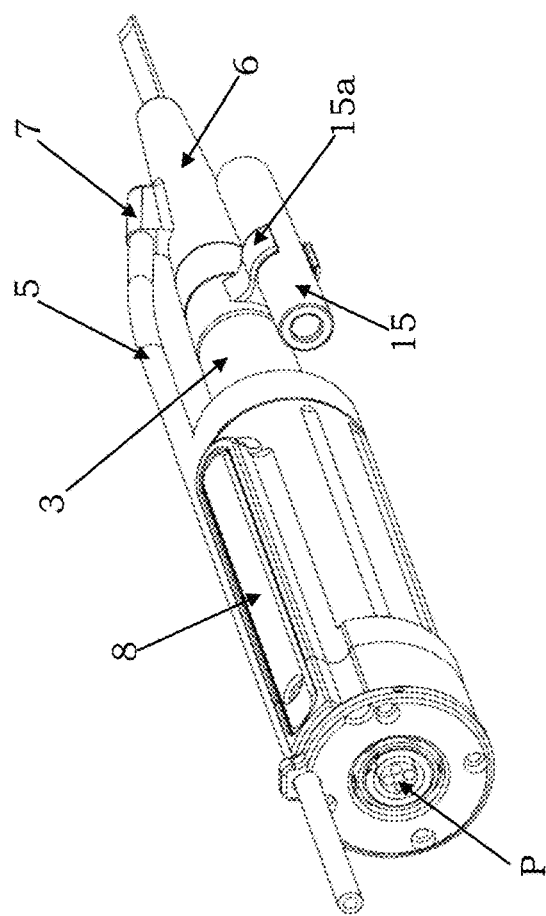
FIG. 3A shows a perspective view of a handset according to an embodiment of the present disclosure.
Figure 3B:
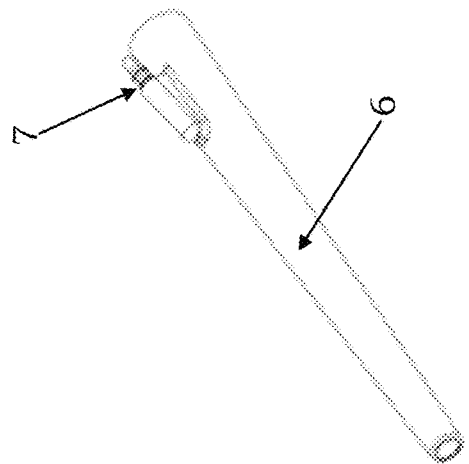
FIG. 3B shows a detail of the handset according to FIG. 3A.

With reference to FIGS. 3A and 3B, in an embodiment, the handset 1 also comprises a second covering element 6 configured to cover at least partially the tool T to be associated with the handset 1.

Conveniently, the second covering element 6 is connected removably to the first covering element 3, for example by means of a snap-action connection or a threaded connection. In this case, during installation of the handset 1, firstly the tool is connected to the horn 2B and then the second covering 6 is connected to the first covering 3.

Still with reference to the embodiment shown in FIGS. 3A and 3B, the second covering element 6 comprises a connection element 7 for the duct 5, such that the proximal end of the duct 5 may be engaged onto this connection element 7. In this way, by means of the connection element 7 with which the duct 5 engages, the cooling medium transported by this duct 5 is able to flow inside the second covering element 6 and reach the tool and the zone to be treated. In this case, the connection element 7 places the inside of the duct 5 in fluid communication with the inside of the second covering element 6.

In other words, the duct 5 has a first distal end connected to the pump and a second proximal end connected to the second covering element 6 by means of the connection element 7, thus allowing the cooling medium to flow into said second covering element and therefore allow effective irrigation of the tool (which is partially covered by this second covering element 6) and the zone to be treated. Conveniently, in this case, the second covering element 6 allows the cooling medium to be conveyed to the tool without the duct occupying the area of the anatomical site and getting in the way of the surgeon when handling the handset 1. Obviously, the length of the second covering element 6, measured along the longitudinal axis H-H. is chosen depending on the tool used.

The embodiment illustrated above (in which the duct 5 is arranged on the outside of the handset body 1' and engages with the second covering element 6 by means of the connection or engaging element 7) must not be understood as limiting the scope of the present disclosure.

For example, with reference again to FIG. 2A it is also possible to envisage a solution in which the duct 5 extends only on the outside of the handset 1 and the second covering element 6 is not necessarily present. In this case, the proximal end of the duct 5 is connected to the handset 1 (for example connected to the first covering element 3) by means of engaging means 5b and is located on the outside of this handset 1 (as shown also in FIGS. 6A and 6C), the fluid being circulated only on the outside of the handset 1.

In an embodiment comprising the engaging element 5b and also the engaging element 5a (as shown for example in FIGS. 6A and 6C), the duct 5 may be rotated about the handset 1 and positioned in the most convenient position depending on the application. In particular, the engaging elements 5a and 5b (which may be in the form of rings provided with a portion for engagement with the duct 5) ensure a flexibility during insertion and stability during use.

In these cases, it may be sufficient to use only the covering element 3, which has suitable grooves for housing the various engaging means and may have a length which varies depending on the requirements and/or circumstances, (in any case such as to protect the horn). The covering element 3 may in any case used for connection to further guides.

In any case, the duct 5 is preferably shaped so as to follow the profile of the handset 1 and therefore so as to reduce the overall dimensions. In this case, as previously mentioned, the space occupied by the duct 5 is reduced owing to the configuration of the handset body 1' which allows the tube to be housed such that it does not interfere with the surgeon's hand. A friction action, which may be provided by means of an O-ring, may help keep the tube in position.

Furthermore, the handset 1 comprises a triggering element, activation of which causes the activation of the ultrasound generating means 2, in particular the generation of ultrasounds by the piezoelectric transducer 2a.

Advantageously according to the present disclosure, the handset 1 also comprises a control lever 8 connected rotatably to the handset body 1' at a given connection point 9. More particularly, the connection point 9 is the fulcrum about which the lever moves (namely the point about which the lever tends to rotate) following the pressure exerted by the surgeon.

The control lever 8 is housed inside a special housing seat 8' formed in the handset body 1'. In the rest configuration where there is no interaction with the surgeon, the control lever 8 is substantially parallel to the longitudinal axis H-H and the ultrasound generating means 2 are not activated.

The control lever 8 is suitably configured to activate the triggering element as a result of its movement about the connection point 9 following the pressure exerted by the surgeon. In this way, once the control lever 8 is displaced from its rest configuration, namely when this lever is moved about the connection point 9, it causes the activation of the triggering element and therefore causes the activation of the ultrasound generating means 2 in the manner described below. In other words, the activation is determined by the rotation of the control lever 8 about its fulcrum (which corresponds to its rotatable connection point on the handset body 1').

In a preferred embodiment, shown in FIG. 4, the triggering element comprises a Hall effect sensor 10 connected to a printed circuit board (indicated hereinbelow simply as PCB) and a magnet 11 arranged on the control lever 8. In this embodiment, the magnet 11 is arranged at one end of the control lever 8, preferably the distal end, while at the opposite end of the lever, substantially at the centre of gravity of the handset 1, there is an elastically deformable element 12 (such as a spring) which connects the control lever 8 to the handset body 1' and is configured to keep this control lever 8 in the rest configuration. The connection point 9 is instead situated between the magnet 11 and the elastically deformable element 12.

In this embodiment, the movement of the control lever 8 around the connection point 9 (with consequent compression of the spring 12) causes a variation of the relative distance between the Hall effect sensor 10 and the magnet 11, and therefore a variation of the magnetic field recorded by this Hall effect sensor 10, causing the activation of the ultrasound generating means 2 once this distance exceeds a predetermined threshold value.

The presence of a LED 13 connected to the PCB is also envisaged, this LED 13 providing an indication of the operative condition of the handset 1. In this case, a light guide 13' which guides the light radiation emitted by the LED 13 along the surface of the handset body 1' is also provided, said light guide 13' protecting at the same time the LED 13 and the other internal electronic components owing also to the arrangement around the guide of a pair of O-rings OR which ensure protection thereof and an optimum seal.

Figure 5:
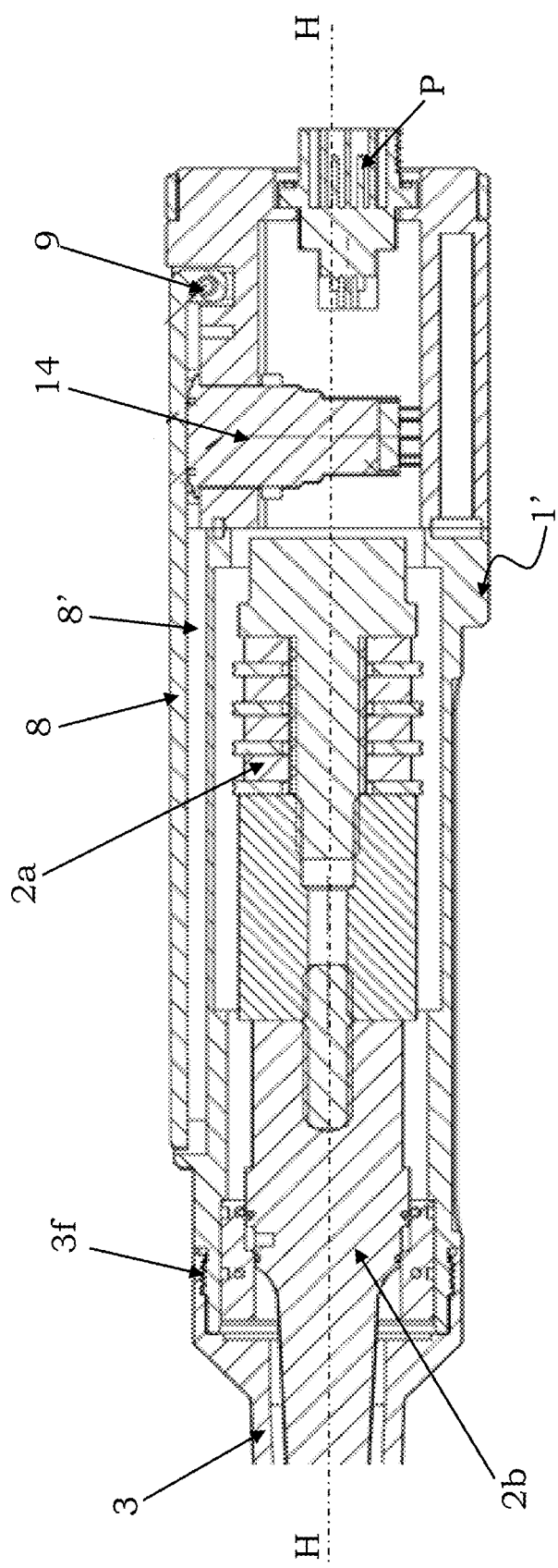
FIG. 5 shows a cross-section through a handset according to an alternative embodiment of the present disclosure.

Alternatively, as shown in FIG. 5, the triggering element is a pushbutton 14 operated by means of a pressing contact with the control lever 8 during the movement thereof about the connection point 9. In this way, pressing the control lever 8 in turn causes it to press against the pushbutton 14 so as to activate the system.

The pushbutton 14 may be for example an IP67 pushbutton with incorporated LED, this LED indicating the operative condition of the handset 1.

In this embodiment, in the rest configuration, the control lever 8 is in direct contact with the top of the pushbutton 14 without exerting any pressure thereon, while, following the pressure exerted by the surgeon on the lever, the pushbutton 14 is pressed causing activation of the ultrasound generating means 2. The connection point 9 is situated at the distal end, so that the pressure exerted by the surgeon is applied at the opposite end of the lever, namely at the centre of gravity of the handset 1. When the pressure is no longer exerted, the pushbutton 14 brings the lever back into the rest configuration.

In all the embodiments, the control lever 8 therefore has the function of transferring the activation point from the distal part to the centre of gravity of the handset 1, simplifying considerably the use and the allowing more comfortable gripping positions during handling.

Figure 4:
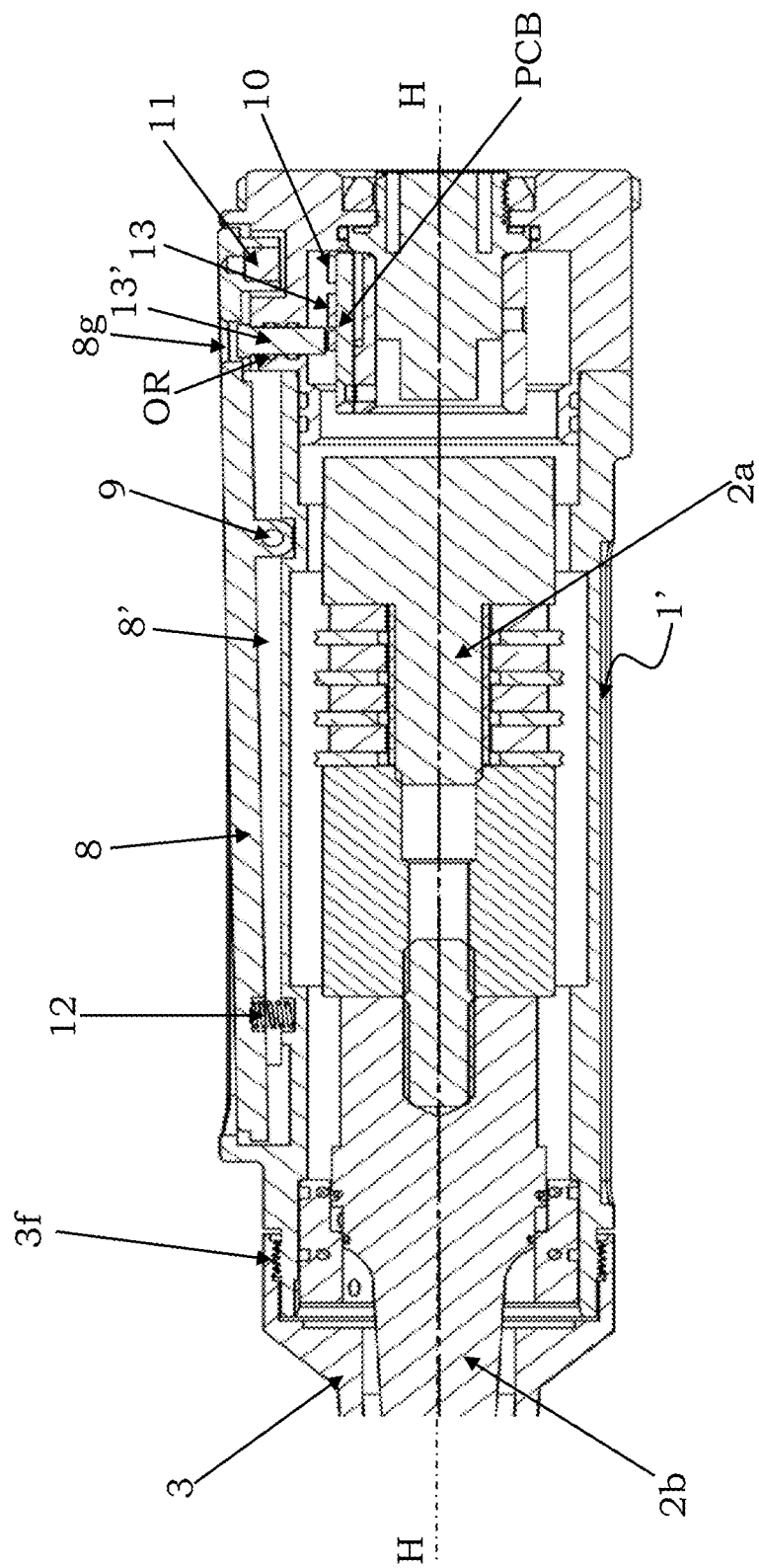
FIG. 4 shows a cross-section through a handset according to an embodiment of the present disclosure.

Furthermore, the PCB, which houses and drives the LED in the embodiment shown in FIG. 4, is present in both the embodiments and generally allows communication between the handset 1 and the generator to which it is connected.

In particular, the handset 1 is provided with a communication circuit (comprising for example a microprocessor) which in turn comprises a memory unit (for example an EEPROM memory) containing all the information useful for identification and operation thereof. For example, the memory unit of the handset 1 may comprise its serial number, which is communicated to the generator, thus allowing immediate identification of the handset. In addition to the handset model, the circuit also comprises a temperature sensor and, in a preferred embodiment, the Hall effect sensor 10 for activation thereof.

The data communication with the generator is managed by a communication buffer using the RS485 standard, in accordance with a preferred embodiment of the present disclosure. The handset thus has its own CPU which maintains the link with the generator by means of a data communication bus.

The socket P allows the transfer of data as well as the supplying of power for the piezoelectric transducer.

As indicated above, the handset 1 also has a luminous signalling element, preferably an LED, which is configured to indicate to the surgeon an operative condition of the handset 1.

Figure 6A:
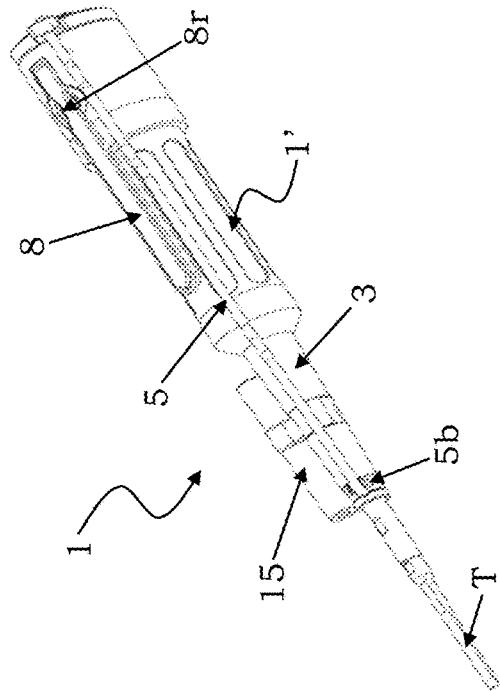
FIGS. 6A to 6B show respectively a perspective view and a detail of a handset according to an embodiment of the present disclosure.
Figure 6B:
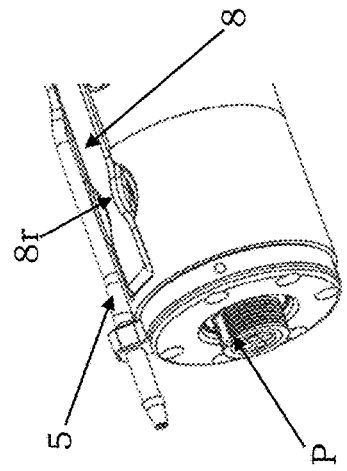
Figure 6C:
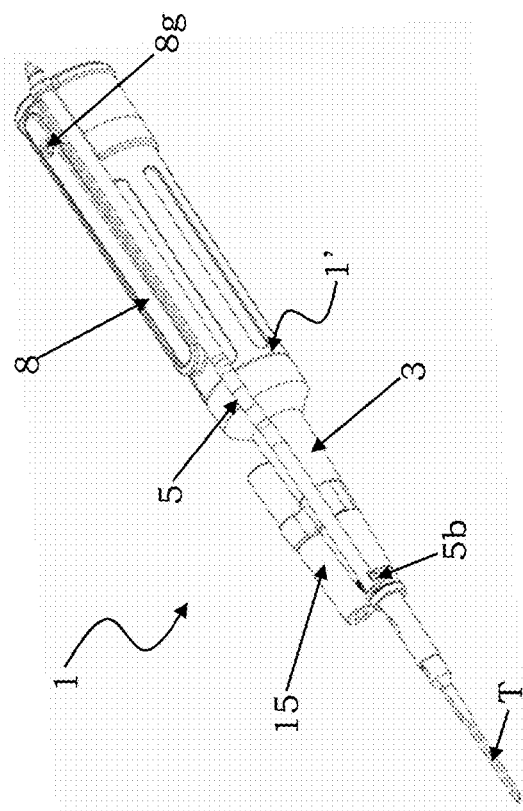
FIGS. 6C to 6D show respectively a perspective view and a detail of a handset according to an alternative embodiment of the present disclosure.
Figure 6D:
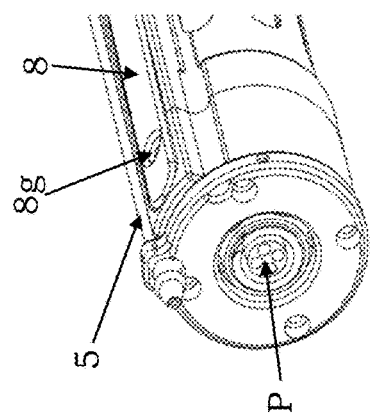

In particular, in the embodiment shown in FIG. 4, the LED 13 is arranged on the PCB and the light emitted is transmitted through the guide 13' which guides the light radiation emitted and allows it to be transmitted through an opening 8g (for example with a circular shape) formed in the control lever 8, as shown in detail in FIGS. 6A and 6B.

In the embodiment shown in FIG. 5, the LED is instead incorporated in the pushbutton 14 and the light emitted is visible since the control lever 8 has a thinner portion 8r opposite this pushbutton 14, this thinner portion 8r allowing the passage of the light emitted by the LED. The thinner portion 8r may be for example realized by removal of material from the sides of the control lever 8 at the point of contact with the pushbutton 14.

In general, the LED of the handset 1 is a LED of the RGB type which may indicate various operating modes or signals to the operator.

Expressed differently, in accordance with the present disclosure, the luminous signalling element is housed inside the handset body 1', while the control lever 8 is suitably shaped so as to transfer the signal emitted by this luminous signalling element.

Obviously, the various embodiments illustrated above must not be regarded as limiting the scope of the present disclosure and the control lever 8 may also be differently shaped, and likewise the luminous signalling element may also be arranged in other positions.

It is also pointed out that the luminous signalling element of the handset 1, in addition to signalling that the system is active, may also be configured to provide feedback in the event of contact occurring between the tool and a very hard material (such as steel, titanium and the like), thus allowing the surgeon to move the tool or interrupt the operation. The luminous signalling element also allows feedback to be provided about the state of the device in general, alerting the surgeon also as to the presence of any faults and malfunctions affecting the generator, the tool and the handset 1 itself.

Furthermore, in order to solve the problem associated with the poor visibility in the treatment zone, the handset 1 comprises a lighting element 15 configured to illuminate this zone.

In a preferred embodiment, the lighting element 15 is connected removably to the handset 1, for example to the first covering element 3, by means of a special engaging element 15*a*.

The covering element 3, in addition to protecting the horn 2*b* from any potentially dangerous accidental contact, therefore also has the function of allowing the lighting element 15 to be connected to the handset 1. Furthermore, the covering element 3 allows fixing of the engaging ring for connection with the duct 5 in the case where this duct 5 extends only on the outside of the handset 1.

In an alternative embodiment not shown in the figures, the lighting element 15 may be incorporated inside the handset 1. It is pointed out that, in the case where the lighting element 15 is removably associated with the handset 1 by means of engagement, the system according to the present disclosure is more flexible since this lighting element 15 may be arranged in the position which most convenient for the particular application. In the case where the lighting element 15 is instead inside the handset 1, the system is more compact, but its flexibility is more limited.

In any case, the lighting element 15 may be a laser or an LED which emits a light beam focussed at the tip of the tool, facilitating the work of the surgeon since it increases the visibility in the operating zone and at the same time acts as a sighting device.

Figure 7A:
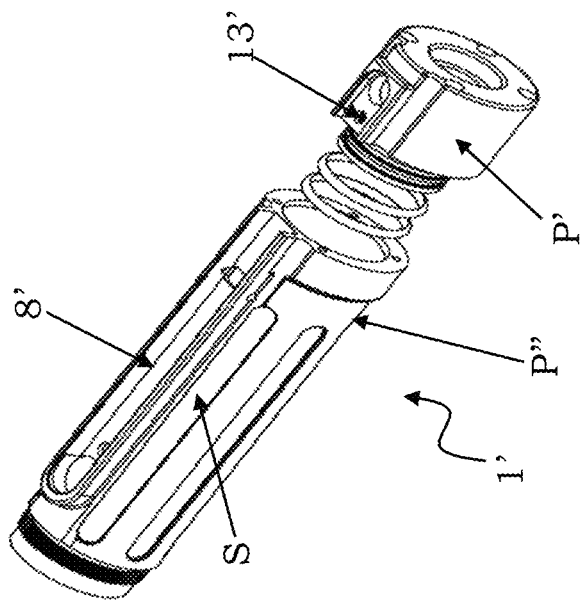
FIGS. 7A and 7B shows a perspective view of a detail of a handset body according to embodiments of the present disclosure.
Figure 7B:
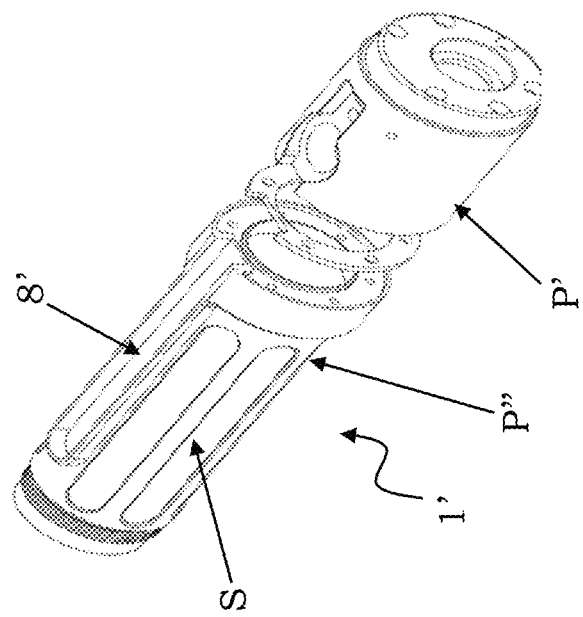

The handset 1 according to the present disclosure is able to ensure an optimum leak-tightness. With reference now to FIGS. 7A and 7B, the handset body 1' is divided into two portions P' (rear cap) and P''' (sleeve) which are suitably connected together in a sealed manner.

In FIG. 7A, which corresponds to the embodiment shown in FIG. 5, the appropriate shape of the cylindrical portions P' and P''' is configured to ensure a better leak-tightness during sterilization, better operating visibility because of the configuration of the control lever 8, and a stable grip due to the presence of the grooves S.

In the solution shown in FIG. 7B, corresponding to the embodiment of FIG. 4, sealing between the two portions P' and P''' is ensured by means of standard O-rings. In particular: the sealing action is provided by means of double O-rings on the front end of the portion P''', on the collar of the horn (namely where the covering element 3 engages), on the portion P', on the light guide 13' and in the region of the socket P.

In both solutions, the grooves S have the function of reducing the weight and ensuring a better gripping action.

In any case, the various embodiments may be combined where possible.

Figure 8A:
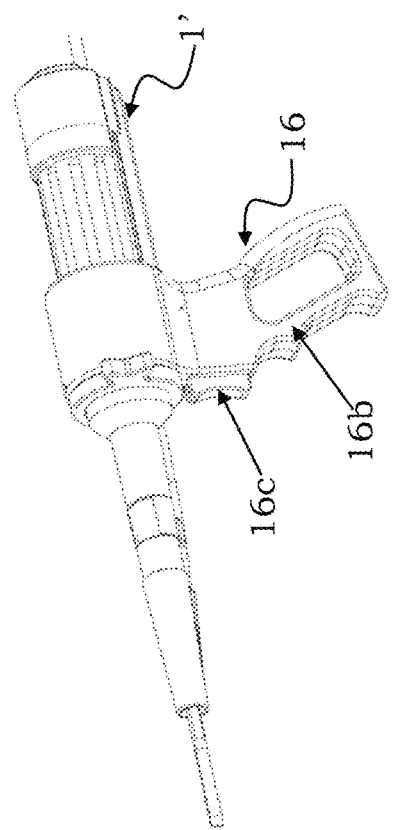
FIG. 8A shows a perspective view of a handset according to an alternative embodiment of the present disclosure.
Figure 8C:
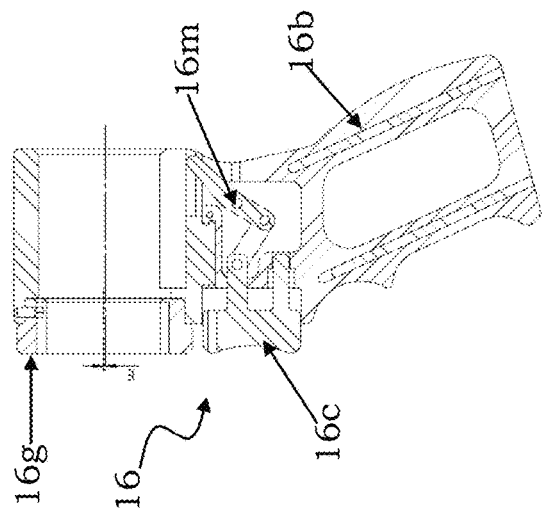
FIGS. 8B and 8C show a perspective view and a cross-sectional view, respectively, of details of the handset according to FIG. 8A.
Figure 8B:
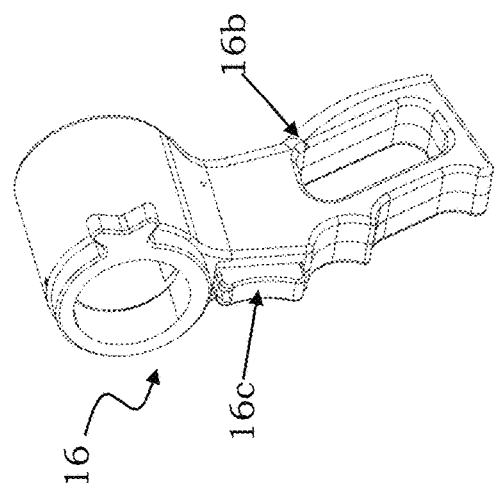

Furthermore, in an embodiment shown in FIGS. 8A-8C, the handset 1 also comprises a gripping system 16 arranged substantially transversely with respect to the handset body 1'.

In particular, the gripping system 16 has a body 16*b*, which forms the handle, and a control element 16*c* (for example a pushbutton) arranged on this body 16*b*, said control element 16*c* being configured to operate a mechanical transmission 16*m* which causes the movement of the control lever 8. In other words, by means of the control element 16*c* (which is for example a pushbutton), the mechanical transmission 16*m* is moved and presses the control lever 8, thus activating the ultrasound generating means 2.

Advantageously, the gripping system 16 is connected removably to the handset body 1', for example by means of a collar arranged on an end of the body 16*b*. In this way, the surgeon is able to choose whether to use the handset with the handle along the longitudinal axis or whether to use the gun-like handle provided by the gripping system 16, thus making the system according to the present disclosure particularly convenient and versatile.

Even more particularly, the mechanical transmission 16*m* is of the cam type with a movement towards the handset body 1', namely from the bottom upwards with local reference to the figures, and is operated by the control element 16*c*.

Furthermore, the removable connection between the gripping system 16 and the handset body 1' is realized by means of an eccentric ring nut 16*g* provided at the top of the body 16*b*.

In accordance with an embodiment shown in FIGS. 9A-9D, the handset 1 further comprises a covering element 17 which is made of silicone and which covers entirely the control lever 8. In particular, the covering element 17 is connected (fixed) to the handset body 1' by means of fixing holes/slots 18, these fixing slots 18 being provided in a shaped profile 19 formed around the control lever 8. In other words, the shaped profile 19 projects from the handset body 1' and surrounds the control lever 8 (it should also be noted that the shaped profile 19 may also be provided in the other embodiments illustrated in the present description). The covering element 17 is positioned so as to protect the control lever 8, allowing at the same time the light from the luminous signalling element to pass through.

Finally, conveniently according to the present disclosure, the ultrasound generating means 2 are configured to transmit ultrasounds both to tools used for the removal of bone cement and to tools used for osteotomy operations. The present disclosure therefore provides a handset able to be connected both to tools for bone cement removal and to tools used for osteotomy, both these operations being performed using the same handset. In this case, the piezoelectric transducer 2*a* is able to provide different power outputs and manage different frequencies so as to be compatible with both applications. This functional feature is obtained by means of a suitable system for controlling the handset 1 provided by the generator.

To conclude, the present disclosure provides a handset for an ultrasonic device having means which allows the handset to be activated in simpler and more efficient manner by the surgeon, while at the same time simplifying handling and use thereof during operations, as well as means which allow the handset to be reconfigured easily, such that it may be adapted to different situations.

Advantageously according to the present disclosure, the handset is such that it may be used by surgeons in a very simple and efficient manner, the form of the handset and the combination of the components used, facilitating the work of the surgeon during operations, in particular allowing simpler handling of the grip piece.

In particular, the combination of the triggering element (such as a pushbutton or a special sensor) and the control lever improves the ergonomic properties of the instrument and allows the surgeon to activate the ultrasound generating means in a much simpler manner, without having to keep a given pushbutton pressed during use and handling of the handset, but by simply operating the control lever. The presence of the control lever arranged along the handset housing therefore allows simple activation of the system in all the different gripping positions during use by the surgeon.

It is pointed out in fact that the handset according to the present disclosure has a handle along its longitudinal axis, and therefore the presence of the control lever, which displaces the activation point also to the centre of gravity of the handset, represents a significant improvement compared to the known solutions, ensuring a more comfortable gripping action and more natural movements for the operator. This improvement is also obtained together with an optimum sealing system.

A further flexible feature of the handset according to the present disclosure is the possibility of converting the axial cylindrical grip into a gun-like grip by means of simple application of a gripping system which is substantially perpendicular to the axis of the handset and has internally a mechanical transmission for activation of the control lever.

The handset according to the present disclosure is also provided with a system for lighting the area to be treated and a duct for supplying a cooling fluid (for example a physiological solution), both these components being associated removably with the handset. In this way, the problem of lighting and cooling the area to be treated is solved, while at the same time ensuring a high degree of versatility and possibility of reconfiguring the handset according to the present disclosure.

Another very advantageous feature is the possibility of managing both the tools for removal of the bone cement and the tools for osteotomy operations using a single handset, further simplifying the system according to the present disclosure.

Finally, it is pointed out that all the features described above, in addition to ensuring easier use by the surgeon, increase the efficiency and the safety of the operation performed using the handset according to the present disclosure.

From the foregoing it will be appreciated that, although specific embodiments of the disclosure have been described herein for purposes of illustration, various modifications may be made without deviating from the spirit and scope of the disclosure, all included in the protection scope as defined by the appended claims.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A handset for an ultrasonic device for bone cement removal and/or osteotomy operations, the handset comprising:
   a handset body which encloses ultrasound generating means comprising at least one piezoelectric transducer and a horn, said handset body extending along a longitudinal axis between a distal end and a proximal end;
   a connection means configured to connect the handset to a tool to which the ultrasounds generated by the ultrasound generating means are transmitted;
   a duct for circulation of a cooling medium, the duct extending at least partially outside the handset;
   a triggering element whose activation causes activation of the ultrasound generating means;
   a control lever coupled to the handset body at a connection point, the control lever being configured to activate the triggering element by means of its movement about the connection point, the control lever comprising an engagement surface configured to be engaged by a user, the engagement surface extending along a longitudinal axis parallel to the longitudinal axis of the handset body, wherein the control lever is housed in a housing seat formed in the handset body;
   a covering element configured to cover at least partially the tool to be associated with the handset, wherein the covering element comprises a connection element for the duct, the connection element being configured so that the duct is placed in fluid communication with an inside of the covering element, the cooling medium being supplied from the duct and flowing inside the covering element; and
   a further covering element configured to cover at least partially the horn, wherein the covering element is removably connectable to the further covering element, and wherein the further covering element is removably connectable to the handset body,
   wherein the covering element and the further covering element are distinct from the handset body.

2. The handset according to claim 1, wherein the triggering element comprises a Hall effect sensor and a magnet arranged on the control lever, wherein the movement of the control lever about the connection point causes a variation of a relative distance between the Hall effect sensor and the magnet, causing the activation of the ultrasound generating means.

3. The handset according to claim 1, wherein the triggering element is a pushbutton and wherein the movement of the control lever about the connection point results in pressing contact of the control lever against said pushbutton, causing the activation of the ultrasound generating means.

4. The handset according to claim 1, wherein the connection means comprise a threaded connection at the end of the horn of the ultrasound generating means.

5. The handset according to claim 1, wherein the duct is removably associated with the handset.

6. The handset according to claim 1, comprising at least one luminous signalling element configured to indicate to the operator an operating condition of the handset.

7. The handset according to claim 6, wherein the luminous signalling element is housed inside the handset body, and wherein the control lever is shaped so as to allow passage of the signal emitted by the luminous signalling element.

8. The handset according to claim 7, wherein the luminous signalling element is a LED incorporated in the triggering element, or wherein the luminous signalling element is a LED connected to a printed circuit board in the handset and radiation emitted by the LED is transmitted by a light guide arranged between the printed circuit board and the control lever.

9. The handset according to claim 1, comprising a lighting element configured to illuminate a treatment zone.

10. The handset according to claim 9, wherein the lighting element is connected removably to the handset.

11. The handset according to claim 1, wherein the handset body has a substantially cylindrical form.

12. The handset according to claim 1, further comprising a silicone covering element configured to cover the control lever, said silicone covering element being connected to the handset body by means of fixing slots.

13. The handset according to claim 1, wherein the ultrasound generating means are configured to transmit ultrasounds both to tools used for the removal of bone cement and to tools used for osteotomy operations.

14. A handset for an ultrasonic device for bone cement removal and/or osteotomy operations, the handset comprising:
- a handset body which encloses ultrasound generating means comprising at least one piezoelectric transducer and a horn, said handset body extending along a longitudinal axis between a distal end and a proximal end;
- a connection means configured to connect the handset to a tool to which the ultrasounds generated by the ultrasound generating means are transmitted;
- a duct for circulation of a cooling medium, the duct extending at least partially outside the handset;
- a triggering element whose activation causes activation of the ultrasound generating means;
- a control lever coupled to the handset body at a connection point, the control lever being configured to activate the triggering element by means of its movement about the connection point, the control lever comprising an engagement surface configured to be engaged by a user, the engagement surface extending along a longitudinal axis parallel to the longitudinal axis of the handset body;
- a covering element configured to cover at least partially the tool to be associated with the handset, wherein the covering element comprises a connection element for the duct, the connection element being configured so that the duct is placed in fluid communication with an inside of the covering element, the cooling medium being supplied from the duct and flowing inside the covering element; and
- a further covering element configured to cover at least partially the horn; and
- a gripping system arranged substantially transversely with respect to the handset body, wherein the gripping system is provided with a control element configured to operate a mechanical transmission which causes the movement of the control lever, and wherein the gripping system is connected removably to the handset body.

15. The handset according to claim 14, wherein the mechanical transmission is of a cam type with a movement towards the handset body and operated by the control element, and wherein the removable connection is formed by an eccentric ring nut provided at a top of a body which forms a handle.

* * * * *